United States Patent [19]

Kawamura et al.

[11] 3,977,861

[45] Aug. 31, 1976

[54] HERBICIDE COMPOSITION

[75] Inventors: Yuji Kawamura; Hiroshi Ono, both of Shiraoka, Japan

[73] Assignee: Nissan Kagaku Kogyo Kabushiki Kaisha, Tokyo, Japan

[22] Filed: Oct. 2, 1974

[21] Appl. No.: 511,372

[30] Foreign Application Priority Data

Oct. 5, 1973   Japan............................ 48-11205

[52] U.S. Cl......................................... 71/92; 71/103
[51] Int. Cl.²........................ A01N 9/22; A01N 9/14
[58] Field of Search................................ 71/92, 103

[56] References Cited
UNITED STATES PATENTS

| | | | |
|---|---|---|---|
| 3,818,026 | 6/1974 | Boesch | 71/92 X |
| 3,836,539 | 9/1974 | Boesch | 71/92 X |
| 3,856,859 | 12/1974 | Moore | 71/103 |

*Primary Examiner*—Joseph Paul Brust
*Attorney, Agent, or Firm*—Brisebois & Kruger

[57] ABSTRACT

A synergistic herbicide composition containing 2-tertiary-butyl-4-(2,4-dichloro-5-isopropyloxyphenyl)-5-oxo-1,3,4-oxadiazoline and 1,1,1-trifluoro-4'-(phenylsulfonyl) methanesulfono-O-toluidine as the active components.

2 Claims, No Drawings

HERBICIDE COMPOSITION

SUMMARY OF THE INVENTION

The present invention relates to a synergistic herbicide composition containing 2-tertiary-butyl-4-(2,4-dichloro-5-isopropyloxyphenyl)-5-oxo-1,3,4-oxadiazoline(hereinafter referred to as G-315) and 1,1,1-trifluoro-4'-(phenylsulfonyl) methanesulfono-0-toluidine(hereinafter referred to as MBR-8251) which has the following formula:

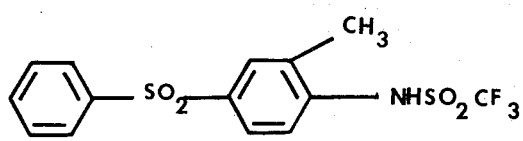

as the active components.

BACKGROUND OF THE INVENTION

G-315 is a herbicide effective on *Panicum Crusgalli* and *Eleocharis acicularis*, which is absorbed and passed through the root, stalk and leaf to exhibit its effect and has a residual effect in the soil for a long period, and MBR-8251 is a novel herbicide for the treatment prior to germination.

*Eleocharis acicularis* and *Panicum Crus-galli* may be given as typical paddy field weeds, but the present situation is such that *Eleocharis acicularis*, which is a perennial weed, is weeded by hand or by machine, that is to say, weeding is carried out during cultivation, or by chemical agents, using MCP (2-methylchlorophenoxy acetic acid), PCP (pentachlorophenol), 2,4,6-trichlor-4'-nitrodiphenylether or a mixture thereof as the herbicide. However when phenoxy herbicides such as MCP etc. are employed, multiplication of the body of the rice-plant may be prevented under certain growing conditions or environmental conditions such as air and water temperature and the like, and rolled leaves of the rice plant may be occasionally formed. Thus, great care is necessary for the use of said herbicides.

Furthermore, after harvest of the rice plants, *Eleocharis acicularis* is removed and 2,4-D MCP, ATA(3-amino-1,2,4-triazole) and a mixture thereof are used. However, when herbicides are sprayed immediately after the termination of the harvest of rice plants, there is usually a problem of labor distribution.

In the control of *Panicum Crus-galli*, a soil-treating agent is used prior to transplantation of the rice plants. After completion of the transplantation, MCC.MCP herbicide (composed of methyl-n-(3,4-dichlorophenyl) carbamate and MCP) and benthiocarb.simetryne herbicide are effective as postemergence stalk and leaf-treating agents around the time when two leaves of *Panicum Crus-galli* have developed. However, after 3 or 4 leaves have developed the effect of these chemical agents is usually reduced.

DETAILED DESCRIPTION OF THE INVENTION

The present invention is based on the discovery that a total weeding effect will be exhibited by the employment of said both compounds in a mixture as compared with the case when they are separately used as a single agent respectively, that no chemical damage is caused on farm crops because they may be used in smaller quantities than the usual quantities when they are separately used and that in this way weeds may be safely, economically and effectively removed. That is to say, they exhibit a precise weeding effect without chemically harming the rice plant.

As the result of a search for a herbicide having a wide period for application by spraying, it was discovered that by using a mixture of G-315 and MBR-8251, while the features of each agent are produced, a mutual effect superior to the effects of the separate agents applied prior to germination or at the beginning of germination of *Eleocharis acicularis* and *Panicum Crus-galli* is exhibited and that the mixture also exhibits a weeds-killing effect on *Sagittaria pygmaea* and *Scirpus Hotarui*, which are difficult to remove with chemical agents.

The herbicide composition of the present invention may be mixed with various carriers and may be applied in powdered, granuled, hydrated, emulsified and flowable form according to the use. Talc, clay, kaolin, diatomaceous earth, calcium carbonate, calcium chlorate, moistened starch, alcohol, benzene, acetone, etc. are used as the carriers. In addition, adjuvants in the production of agricultural chemicals for instance, developing agents, emulsifiers, surface active agents and the like may be used, being added as needed.

The preparations may be used not only as they are but also mixed with fungicides, other herbicides, insecticides etc. and further they may be applied in a mixture with fertilizers.

In order to clarify the functions of the herbicide composition according to the present invention they will be explained in detail the following tests.

Test 1

Removal effect on *Panicum Crus-galli*

Paddy field soil was introduced into Wagner pot of 1/5000 are (an are is 100 square meters) adjusted to a watered condition with a water-depth of 4 cm and 50 grains per pot of *Panicum Crus-galli* seed were sown.

In the pre-emergence treatment, pots were then treated immediately. In the post-emergence treatment the number of the weeds was reduced to 25 per pot when *Panicum Crus-galli* grew to the stage of about 2.5 leaves, then the prescribed amount of a sample chemical agents was diluted with water and dropped on the water-surface by pipette to treat the weeds. The test chemical agents used were commercially available 12% emulsion of G-315, mixed with MBR-8251 in powdered formulation which had been prepared according to the following procedure.

| MBR-8251 50% powdered formulation | |
|---|---|
| MBR-8251 original material | 50 parts by weight |
| Calcium ligninsulfonate | 2 parts by weight |
| Clay | 45 parts by weight |
| Newlexpowder (produced by Nippon Oils & Fats Co., Ltd.) | 3 parts by weight |

The above components are mixed and pulverized to be a hydrated agent. After the treatment by the chemical agents, the pots were placed in a green house (glass house) for three weeks and kept in their watered condition, the above-ground parts of *Panicum Crus-galli* germinated and grown were cut out and weighed. The proportion of the weight thereof to the weight of the corresponding untreated *Panicum Crus-galli* was then calculated.

The test was repeated three times and the average value was calculated. The results are shown in Table 1.

Test 2

Removal effect on *Scirpus Hotarui*

As in Test 1, 50 grains per pot of *Scirpus Hotarui* seed were sown and weed-killing effects by various chemical agents were observed when treated prior to germination and at their grown stage (3 to 4 leaves-period). The number of residual weed plants was examined a month after the treatment and the proportion to that when untreated was calculated. The test was repeated three times to yield the average value. The results are as shown in Table 1.

Test 3

Herbicidal effect on *Eleocharis acicularis*

Paddy field soil was placed into a Neubauer pot of 1/100 m², surface paddy field soil in which *Eleocharis acicularis* had been growing was taken from the ground during winter, stored at low temperature, cut into 3 cm square portions and buried shallowly in the above mentioned soil in the Neubauer pot. The pot was then watered to a water-depth of 2 cm. In the preemergence treatment, this soil was immediately treated. In the postemergence treatment, the plants were grown for three weeks in the green house and then the dropwise-treatment of chemical agents was carried out as in Test 1. 50 days after the treatment by the chemical agents the above-ground parts of *Eleocharis acicularis* were carefully cut, their weights when air-dried were weighed and the proportions of their weight to that of the corresponding untreated *Eleocharis acicularis* were calculated. The test was repeated three times and the average values were calculated. The results are as shown in Table 1.

Test 4

Weed-killing effect on *Sagittaria Pygmaea*

Infant plants of *Sagittaria Pygmaea* (period of 1 to 2 leaves) which had been individually germinated from tubers under watered state were transplanted to a Wagner-pot of 1/5000 are with 5 plants per pot. At the stage of 3 to 4 leaves, diluted aqueous solutions of the chemical agents in the prescribed amount were dropped on the surface of the water by pipette. 50 days after the treatments by the chemical agents, the above-ground parts were cut and their weights in air-dried state were determined. Thereafter, the proportions to those when untreated were calculated. The test was repeated twice and the average values was calculated. The results are a shown in Table 1.

Table 1

| Sample Chemicals | Amount used for treatment g/a (grams per are) | Test 1 *Panicum Crus-galli* Weight of plant body (%) | | Test 2 *Scirpus-Hotarui* Number of plants (%) | | Test 3 *Eleocharis acicularis* Air-dried weight (%) | | Test 4 *Sagittaria pygmaea* Air-dried weight (%) |
|---|---|---|---|---|---|---|---|---|
| | | Pre-germination treatment | Treatment during growth | Pre-germination treatment | Treatment during growth | Pre-germination treatment | Treatment during growth | Treatment during growth |
| G-315 | 0.75 | 23 | 105 | 96 | 102 | 82 | 99 | — |
| used | 1.5 | 8 | 81 | 103 | 106 | 43 | 86 | 92 |
| single | 3 | 0 | 59 | 89 | 94 | 8 | 39 | 110 |
| | 6 | 0 | 18 | 75 | 98 | 0 | 27 | 98 |
| | 12 | — | — | — | — | — | — | 85 |
| MBR-8251 | 1.5 | 36 | 94 | 90 | 99 | 64 | 89 | — |
| used | 3 | 10 | 94 | 52 | 99 | 22 | 77 | 88 |
| single | 6 | 0 | 85 | 16 | 66 | 0 | 63 | 61 |
| | 9 | 0 | 46 | 0 | 34 | 0 | 45 | 40 |
| | 18 | — | — | — | — | — | — | 27 |
| G-315 | 0.75+1.5 | 0 | 40 | 58 | 100 | 13 | 86 | — |
| | 0.75+3 | 0 | 30 | 27 | 97 | 0 | 49 | — |
| + | 0.75+6 | 0 | 13 | 0 | 44 | 0 | 11 | — |
| MBR-8251 | 1.5+1.5 | 0 | 60 | 19 | 38 | 2 | 52 | — |
| used in a | 1.5+3 | 0 | 11 | 0 | 17 | 0 | 33 | 69 |
| mixture | 1.5+6 | 0 | 9 | 0 | 3 | 0 | 9 | 34 |
| | 1.5+9 | — | — | — | — | — | — | 15 |
| G-315 | 3+1.5 | 0 | 33 | 0 | 21 | 0 | 20 | — |
| | 3+3 | 0 | 10 | 0 | 6 | 0 | 16 | 50 |
| | 3+6 | 0 | 3 | 0 | 2 | 0 | 6 | 31 |
| + | 3+9 | — | — | — | — | — | — | 12 |
| MBR-8251 | 6+3 | — | — | — | — | — | — | 28 |
| used in a | 6+6 | — | — | — | — | — | — | 14 |
| mixture | 6+9 | — | — | — | — | — | — | 3 |
| Untreated | — | 100 | 100 | 100 | 100 | 100 | 100 | 100 |

In Test 1 in Table 1, G-315 and MBR-8251 exhibit strong weed-killing effect in the pre-germination treatment on *Panicum Crus-galli* even when they were used individually as a single agent, but the weed-killing effect is further mutually promoted by use of them mixed together and *Panicum Crus-galli* is completely killed by extremely small amounts of the mixture. This tendency is further significant in the postemergence treatment. By individual employment of them hardly any effect is apparent but by combining both of them together a further remarkable growth-prohibiting effect is recognized.

*Scirpus Hotarui* in Test 2 is a weed which has recently posed an important problem because it can't be completely removed by any of the commercially available herbicides. Even G-315's herbicidal effect on the weed is weak and when G-315 alone is used in the preemergence treatment on the weed, the growth of the weed is only temporarily prevented. Hardly any effect is recognized in the postemergence treatment. As compared to G-315, MBR-8251 exhibits slightly greater effects but there is insufficient effect when the chemical is applied in an amount of less than 6 g/are in the preemergence treatment. In the postemergence treatment even when 9 g/are was used, about one-third of the *Scirpus Hotarui* seed was germinated. However weed-killing effect was significantly promoted by the use of both the chemicals in a mixture, especially in the preemergence treatment where complete weed-killing effect was exhibited using half as much MBR-8251 as when it was used as a single agent and significant mutual effect was exhibited.

Both G-315 and MBR-8251 exhibited remarkably high weed-killing effect against *Eleocharis acicularis* in Test 3 in the preemergence treatment but in the postemergence treatment the effect was noticeably reduced. In particular, G-315 was G-315 to have a growth-prohibiting effect until three weeks after treatment but thereafter the weeds recovered and two months after treatment no distinction was recognized from the untreated weeds even if 6 g/are had been applied.

On the other hand, when both the chemical agents were used in a mixture, the weed-killing effect was significantly promoted, and in the preemergence treatment, just as with *Scirpus Hotarui* in Test 2, *Eleocharis acicularis* was completely dried and killed by the combination of both the chemical agents in extremely small amounts. Even in the postemergence treatment its growth was prohibited for a long time and multiplication of *Eleocharis acicularis* was prevented. From these facts its sufficient utility was recognized.

The widespread growth of *Sagittaria pygmaea* of Test 4 in recent years is remarkable and it is a perennial weed in rice-fields, which is as hard to remove as *Scirpus Hotarui*.

As shown in Table 1, G-315 has only a slight growth-prohibiting effect even when employed in an amount twice that in practice. For MBR-8251 no effect can be expected unless a large amount of it is applied.

However, as shown in Table 1, by the use of a mixture of both agents, the growth-prohibiting effect was mutually increased and multiplication of weeds was significantly prohibited.

That is to say, when MBR-8251 was used singly, no growth-prohibiting effect was recognized, but it is shown that using it as a mixture in the amount of 6 to 9 g/are with a small amount of G-315 the growth and multiplication of *Sagittaria pygmaea* may be almost completely prohibited. The above tests were conducted in pots but in order to demonstrate the usefulness of the herbicide composition according to the present invention field-tests were also conducted.

Test 5

Field-Test

The chemical agents were applied just before harrowing and leveling in a submerged rice-field on the 14th of May. In the section where G-315 was used singly, a commercially available 12% emulsion and a granular agent hereunder prepared was applied. In the section where MBR-8251 was used singly, a flowable preparation hereinafter described and a granular agent was applied and in the section where G-315 and MBR-8251 were used together in combination, the flowable preparation of Examples 1 and 2 and the granular agent were respectively used. The treatment by mixing the chemical agents with the soil was carried out at the time of smoothing the soil in preparation for rice-plant transplantation. The emulsion was diluted with water to a prescribed concentration and applied to the surface of the water. The flowable preparation was dropped by pipette, in its original liquid form, onto the surface of the water. 4 days after the harrowing and leveling in a submerged rice-field, the water was withdrawn, dashboards between the sections were taken out and rice-plants belonging to the 2.2 to 2.8 leaves period were transplanted using a Kubota's two-lines rice-plant transplanting machine. The granular agent was scattered by hand on the 5th day after the transplantation in an applied amount of 3 kg/10 are. The test section was 4 m by 4 m and was partitioned off by dashboards and each section was repeated twice. Observation of their effects on rice-plants was conducted by the human eye and their weed-removal effects were judged by the following standard after two months had passed since the rice-plant transplantation.

| Standard for the judgement of Weed-Removal Effect | |
|---|---|
| − | no effect |
| + | small effect |
| ++ | medium effect (about ½ to ⅓ of the amounts by weight of the germinated and of the grown weeds to those in the untreated section) |
| +++ | great effect (less than ⅛ of the amounts by weight of the germinated and of the grown weeds to those in the untreated section) |
| × | extremely great effect-weeds are completely killed |

Composition of Sample Chemical agents

| MBR-8251 Flowable | |
|---|---|
| MBR-8251 original material | 24 parts by weight |
| Sorpol 9838 (a registered Trade Mark) | 7 parts by weight |
| Water | 69 parts by weight |
| MBR-8251 Granular agent | |
| MBR-8251 original material | 5 parts by weight |
| Clay | 80 parts by weight |
| Bentonite | 15 parts by weight |
| G-315 Granular Agent | |
| G-315 original material | 2 parts by weight |
| Clay | 83 parts by weight |
| Bentonite | 15 parts by weight |

The results are shown in Table 2.

Table 2

| Treating method | Sample Chemical agents | Amount to be supplied for treatment g/a | Weed-Removal Effect (2 months after rice-plant transplantation) | | | | | Influences on rice plant |
|---|---|---|---|---|---|---|---|---|
| | | | *Panicum Crusgalli* | Perennial weeds* | *Scirpus Hotarui* | *Eleocharis acicularis* | *Sagittaria pygmaea* | |
| Mixing treatment before harrowing and leveling in | G-315 Emulsion | 6 | × | × | + | +++ | − | Top parts of leaves were slightly color-changed |
| | MBR-8251 (Flow- | 8 | +++~× | +~++ | ++ | +++ | − | |

Table 2-continued

| Treating method | Sample Chemical agents | Amount to be supplied for treatment g/a | Weed-Removal Effect (2 months after rice-plant transplantation) | | | | | Influences on rice plant |
|---|---|---|---|---|---|---|---|---|
| | | | Panicum Crusgalli | Perennial weeds* | Scirpus Hotarui | Eleocharis acicularis | Sagittaria pygmaea | |
| sub-merged rice field | able) | 12 | x | ++ | +++ | x | — | Slight prohibition of growth at the beginning stage |
| | | 20 | x | ++ | x | x | ++ | Prohibition of growth |
| | G-315 + MBR-8251 (Flowable) | (1) 4+8 | x | x | x | x | +++ | |
| | | (2) 4+12 | x | x | x | x | +++ | Slight prohibition of growth at the beginning stage |
| Treatment after rice-plant transplantation | G-315 Emulsion | 6 | x | x | +~++ | ++ | — | Top parts of leaves where slightly color-changed |
| | MBR-8251 Granular Agent | 15 | x | ++ | ++ | ++ | ++ | Slight prohibition of growth at the beginning stage |
| | | 21 | x | ++ | +++~x | +++ | ++ | Prohibition of growth |
| | G-315 + MBR-8251 (Granular Agent) | (1) 4.5+9 | x | x | x | x | +++ | |
| | | (2) 4.5+15 | x | x | x | x | +++~x | Slight prohibition of growth at the beginning stage |
| | Untreated | | — | — | — | — | — | |

NOTE *The perennial weeds were *Cyperus difformis, Monochoria Vaginalis, Lindernia pyxidaria, indica, Doparium junceum* and *Ludwigia prostrata*.

On the test field used in the previous field test, large amounts of seeds of *Scirpus Hotarui* and tubers of *Sagittaria pygmaea*, both of which are difficult to remove, were scattered and the effects on them were investigated, together with those on *Panicum Crus-galli, Cyperus difformis, Monochoria vaginalis, Lindernia pyxidaria, Rotals indica, Elatine triandra* and *Eleocharis acicularis* and so on, which grew naturally.

As stated in Table 2, when the chemicals were used singly no effective results were obtained on *Sagittaria pygmaea, Eleocharis acicularis* and *Scirpus Hotarui*, regardless of the difference between the methods used.

Particularly when 12 g/are of MBR-8251 was applied in the granular agent section, chemical damage such as growth-prohibiting action on the rice plant was recognized. On the contrary, in the sections where both chemicals were together used in combination, not only was significant growth prohibiting action recognized on *Sagittaria pygmaea* but also on all other kinds of weeds complete weed-killing effect was exhibited with almost perfect results and without any chemical damage caused thereby.

Examples relating to the present invention are as follows.

| Example 1 | Flowable (1) | |
|---|---|---|
| | G-315 original material | 8 parts by weight |
| | MBR-8251 original material | 16 parts by weight |
| | Sorbol 9838 (a registered Trade Mark by Toho Chemical Industries Co., Ltd.) | 7 parts by weight |
| | Water | 69 parts by weight |

The above components were uniformly mixed to obtain a Flowable.

| Example 2 | Flowable (2) | |
|---|---|---|
| | G-315 original material | 8 parts by weight |
| | MBR-8251 original material | 24 parts by weight |
| | Sorbol 9838 (a registered Trade Mark) by Toho Chemical Industries Co., Ltd.) | 7 parts by weight |
| | Water | 61 parts by weight |

The above components were uniformly mixed to a Flowable.

| Example 3 | Granular Agent (1) | |
|---|---|---|
| | G-315 original material | 1.5 parts by weight |
| | MBR-8251 original material | 5.0 parts by weight |
| | Clay | 78.5 parts by weight |
| | Bentonite | 15.0 parts by weight |

The above components were uniformly mixed and pulverized, then a small amount of water was added, followed by agitation, mixing, kneading and granulation through an extrusion granulator to produce granules. The granules were then dried to form a granular agent.

| Example 4 | Granular Agent (2) | |
|---|---|---|
| | G-315 original material | 1.5 parts by weight |
| | MBR-8251 original material | 3.0 parts by weight |
| | Clay | 80.5 parts by weight |
| | Bentonite | 15.0 parts by weight |

The above components were uniformly mixed and pulverized, a small amount of water was added, followed by agitation, mixing, kneading, and then granulation through an extrusion granulator to produce granules. The granules were then dried to form a granular agent.

What is claimed is:

1. A synergistic herbicidal composition characterized by containing
   a. 2-tertiary-butyl-4-(2,4-dichloro-5-isopropyloxy-phenyl)-5-oxo-1,3,4-oxadiazoline and
   b. 1,1,1-trifluoro-4'-(phenylsulfonyl) methanesulfono-O-toluidine as the active components, and in which the ratio of (a) to (b) is 1:0.5 to 1:8.

2. A method for terminating the life cycle of higher plants which comprises contacting said plants with an effective amount of a synergistic herbicide composition containing
   a. 2-tertiary-butyl-4-(2,4-dichloro-5-isopropyloxy-phenyl)-5-oxo-1,3,4-oxadiazoline and
   b. 1,1,1-trifluoro-4'-(phenylsulfonyl methanesulfono-O-toluidine as the active components, and in which the ratio of (a) to (b) is 1:0.5 to 1:8.

* * * * *

UNITED STATES PATENT OFFICE
CERTIFICATE OF CORRECTION

PATENT NO. : 3,977,861
DATED : August 31, 1976
INVENTOR(S) : YUJI KAWAMURA and HIROSHI ONO It is certified that error appears in the above–identified patent and that said Letters Patent are hereby corrected as shown below:

[30] Foreign Application Priority Data

Oct. 5, 1973   Japan.................. 48-112052

Signed and Sealed this

Twenty-fifth Day of January 1977

[SEAL]

Attest:

RUTH C. MASON
*Attesting Officer*

C. MARSHALL DANN
*Commissioner of Patents and Trademarks*